(12) United States Patent
Long

(10) Patent No.: US 11,730,518 B2
(45) Date of Patent: *Aug. 22, 2023

(54) SUBAXILLARY TRACTION DEVICE TO ADDRESS SHOULDER DYSTOCIA DURING CHILDBIRTH

(71) Applicant: William H. Long, Jacksonville, FL (US)

(72) Inventor: William H. Long, Jacksonville, FL (US)

(*) Notice: Subject to any disclaimer, the term of this patent is extended or adjusted under 35 U.S.C. 154(b) by 831 days.

This patent is subject to a terminal disclaimer.

(21) Appl. No.: 16/548,238

(22) Filed: Aug. 22, 2019

(65) Prior Publication Data

US 2019/0374256 A1 Dec. 12, 2019

Related U.S. Application Data

(63) Continuation of application No. 15/196,458, filed on Jun. 29, 2016, now Pat. No. 10,398,472.

(51) Int. Cl.
*A61B 17/00* (2006.01)
*A61B 17/44* (2006.01)

(52) U.S. Cl.
CPC .. *A61B 17/442* (2013.01); *A61B 2017/00438* (2013.01); *A61B 2017/00862* (2013.01)

(58) Field of Classification Search
CPC ........ A61B 17/442; A61B 2017/00438; A61B 2017/00862
See application file for complete search history.

(56) References Cited

U.S. PATENT DOCUMENTS

2004/0059368 A1* 3/2004 Maryanka ............. A61M 29/00
606/191
2016/0157647 A1* 6/2016 Rampersad ........... A61F 13/105
294/25

FOREIGN PATENT DOCUMENTS

EP 1132021 A1 * 9/2001 ............. A45D 44/18

* cited by examiner

*Primary Examiner* — Steven O Douglas
(74) *Attorney, Agent, or Firm* — Camille A. Wilson; Wilson Dutra, PLLC

(57) ABSTRACT

A subaxillary traction device having an elongated body portion with a first end and a second end, at least one receptacle member disposed on the first end defining a cavity to receive a fingertip, a handle opening disposed adjacent or near the first end and a handle opening disposed adjacent or near the second end, the handle openings being of sufficient size to receive at least one finger there through, whereby the body portion is positionable under the posterior axilla of a fetus experiencing shoulder dystocia such that traction may be applied allowing delivery of the posterior aim affecting the safe delivery of the baby.

8 Claims, 2 Drawing Sheets

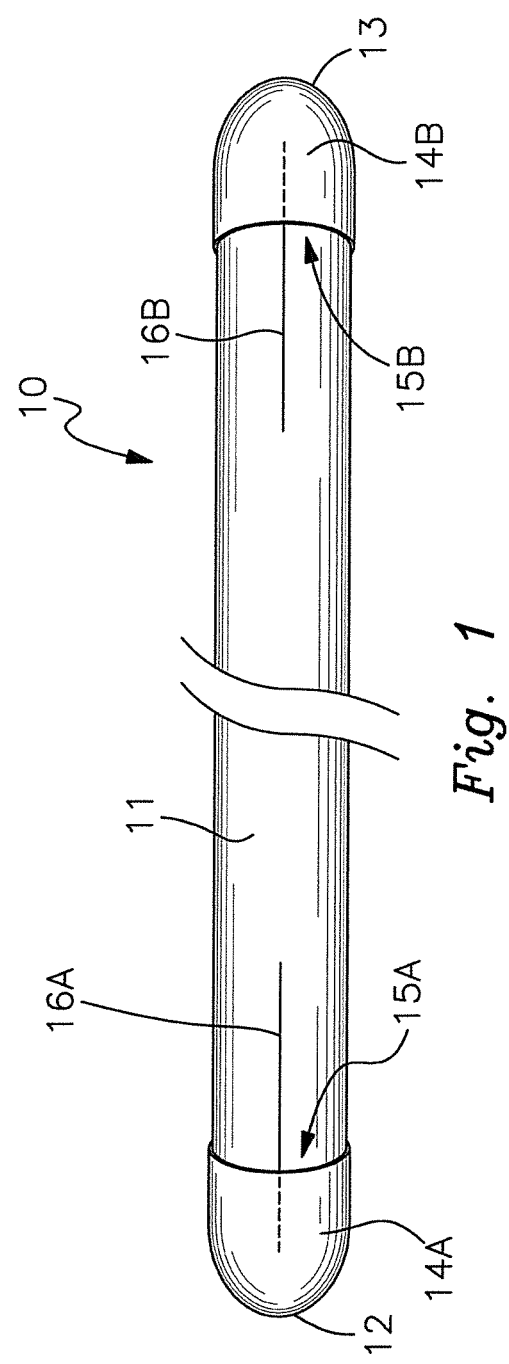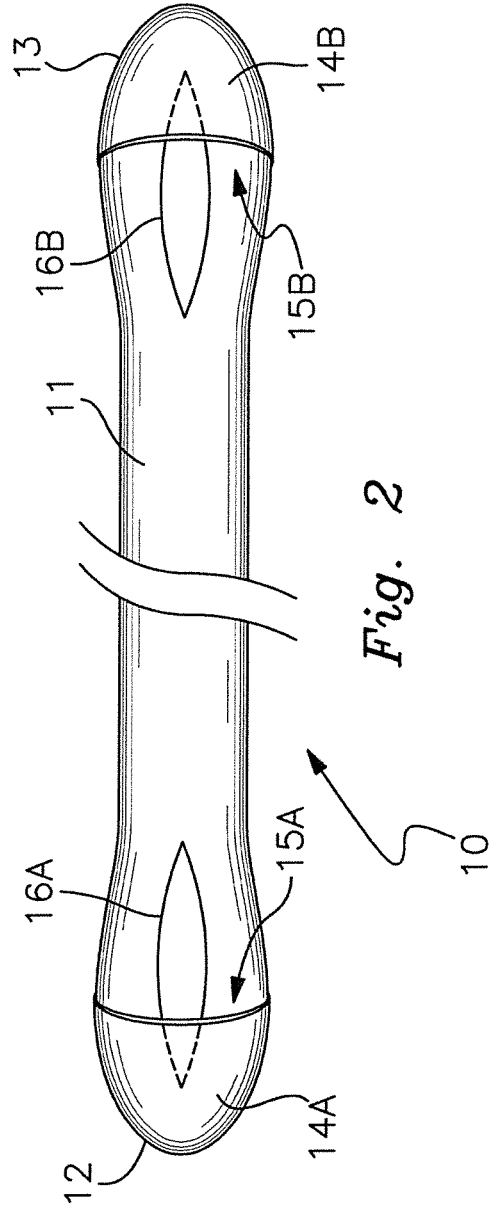

SUBAXILLARY TRACTION DEVICE TO ADDRESS SHOULDER DYSTOCIA DURING CHILDBIRTH

BACKGROUND OF THE INVENTION

Shoulder dystocia is a serious and unpredictable obstetrical complication that occurs during childbirth when the shoulders of the fetus become entrapped behind the mother's pubic bone and sacrum. It is a true obstetrical emergency requiring a rapid and effective remedy or serious injury to the mother or baby may occur. The greatest concern is the over stretching of the nerves from the fetal neck to the fetal arm (brachial plexus). Over stretching of these nerves may cause permanent nerve injury leading to paralysis of the affected limb (Erbs palsy). A variety of techniques have been described to deal with such an emergency. Most of these involve some traction on the fetal head and neck that may injure the brachial plexus.

Another technique involves delivery of the posterior arm of the fetus. Traction beneath the fetus's posterior axilla (arm pit) may assist in this maneuver by "shrugging" the baby's shoulder, reducing the anterior and posterior (front to back) diameter of the fetal shoulder girdle. This shrugging allows greater access to the posterior arm of the infant and makes easier the delivery of the posterior arm. Once this is accomplished, safe delivery of the infant is possible.

This technique has been improved by utilizing a length of catheter tubing as a traction device. In the standard methodology, the tubing is looped over the obstetrician's index finger, the looped end is inserted trans-vaginally beneath the fetus' posterior axilla, and the looped end is then transferred to the opposite index finger and pulled to create a sling under the fetus' axilla and around the shoulder. Because the tubing is slippery, the exposed ends of the tubing are then typically knotted or clamped. Traction is then applied to the sling shrugging the posterior shoulder assisting in the delivery of the fetal posterior arm.

It is an object of this invention to improve upon the manipulation technique by providing a subaxillary traction device having improved structural and functional characteristics in comparison to the length of tubing currently utilized. The traction device provides a structure that increases the ease and efficiency of transvaginal insertion and positioning of the device beneath the posterior axilla and of retrieving the inserted end of the device. The traction device further provides a handle or grip structure that enables traction to be applied using the fingers without needing to form a knot or utilize a clamp.

SUMMARY OF THE INVENTION

The invention in general is a subaxillary traction device to address shoulder dystocia during childbirth, a condition in which the head of the fetus passes into the birth canal but the shoulders of the fetus become lodged between the mother's pubic bone and sacrum. The invention is a device utilized in a posterior axillary manipulation technique, wherein the posterior arm of the fetus is pulled through the birth canal, thereby rotating and slanting the shoulders of the fetus such that delivery of the fetus is no longer impeded. For the purposes of this disclosure, the term "obstetrician' shall be used to designate the user of the traction device, but it is to be understood that this term is meant to be inclusive of any doctor, nurse or other medical personnel that might be utilizing the traction device.

In various embodiments, the subaxillary traction device is a thin or small diameter elongated member composed of a flexible material, such as for example a biocompatible silicone polymer. The elongated body portion of the traction device may be formed as a generally strap-like, cylindrical or tubular structure. One or preferably both ends of the traction device comprise a hood or cup-like receptacle member that is closed on the end and open in the direction toward the middle of the body portion of the device, the receptacle forming a finger-receiving cavity sized to securely receive the end of the obstetrician's finger. Most preferably, a short slit, slot, aperture or opening is positioned adjacent or near each end of the body portion, the openings in the elongated body portion sized such that one or more fingers may be placed through the openings to apply traction to the device once it has been looped beneath the posterior axilla. The openings thereby form handles to preclude slipping of the device when traction is applied to shrug the posterior shoulder, allowing one to draw the posterior arm through the birth canal.

In alternative language the invention in various embodiments is a subaxillary traction device adapted to address the problem of shoulder dystocia during childbirth by placing beneath the posterior axilla of a fetus, the subaxillary traction device comprising an elongated body portion having a first end and a second end, said body portion composed of a flexible, pliable polymer material suitable for use in a medical or surgical procedure; and a first receptacle member disposed on said first end, said first receptacle member having a cavity sized and configured to receive and retain a fingertip. The invention may further comprise a pair of handle openings disposed on said body portion; wherein one of said handle openings is disposed adjacent or near said first end and another of said handle openings is disposed adjacent or near said second end; a second receptacle member disposed on said second end; a second receptacle member disposed on said second end, said second receptacle member having a cavity sized and configured to receive and retain a fingertip; wherein said handle openings are configured as slits, slots or apertures; wherein said handle openings are sized to receive at least one finger therethrough; wherein said first receptacle member is closed at said first end of said body portion and open in the direction of said second end of said body portion; wherein said second receptacle member is closed at said second end and open in the direction of said first end of said body portion; wherein said body portion is composed of a silicone material; wherein said body portion is configured as a strip, strap, cylindrical member or tubular member; wherein said body portion is approximately 60-80 cm in length and approximately 5-10 mm in width or diameter; wherein said receptacle members are approximately 2-4 cm in length; and/or wherein said handle members are approximately 6-10 cm in length.

Alternatively still, a subaxillary traction device adapted to address the problem of shoulder dystocia during childbirth, the sub axillary traction device comprising an elongated body portion having a first end and a second end, said body portion composed of a flexible, pliable polymer material suitable for use in a medical or surgical procedure; a pair of handle openings disposed on said body portion; and a first receptacle member disposed on said first end, said first receptacle member having a cavity sized and configured to receive and retain a fingertip; wherein said traction device is configured such that said body portion is placed beneath the posterior axilla of a fetus experiencing shoulder dystocia during birth such that said first end and said second end are accessible to apply traction to the posterior axilla; wherein one of said handle openings is disposed adjacent or near said first end and another of said handle openings is disposed adjacent or near said second end; further comprising a second receptacle member disposed on said second end, said second receptacle member having a cavity sized and configured to receive and retain a fingertip; and/or wherein said handle openings are configured as slits, slots or apertures.

Alternatively still, the invention is a method of treating should dystocia during childbirth comprising the steps of providing a subaxillary traction device comprising an elongated body portion having a first end and a second end, said body portion composed of a flexible, pliable polymer material suitable for use in a medical or surgical procedure; a pair of handle openings disposed on said body portion; and a first receptacle member disposed on said first end, said first receptacle member having a cavity sized and configured to receive and retain a fingertip; inserting a fingertip into said first receptacle member and introducing said first end of said body portion into a vagina and around a posterior axilla of a fetus; grasping said first end of said body portion, removing said fingertip from said first receptacle member and retrieving said first end from said vagina such that said body portion remains positioned around the posterior axilla; inserting fingers through said handle openings and applying traction to said body portion, thereby flexing and shrugging the shoulder of the fetus to free the fetus; and pulling the posterior arm from the vagina whereby the fetus may be fully removed from the vagina.

Alternatively still, the invention is a subaxillary traction device assisting a surgeon in addressing the problem of shoulder dystocia during childbirth by providing a device to flex a shoulder of a fetus in a womb, the subaxillary traction device comprising or consisting essentially of: a single, elongated body portion having two ends, said body portion composed of a flexible, pliable polymer material suitable for use in a medical or surgical procedure, wherein said body portion has a form chosen from the group of forms consisting of a strip, a strap, a cylindrical member and a tubular member; a first receptacle member disposed on one of said ends, said first receptacle member being closed at said one of said ends of said body portion and open in the direction away from said one of said ends of said body portion, said first receptacle having a cavity sized and configured to receive and retain a fingertip; said body portion having an opening in each of said ends, each of said openings extending through said body portion and sized to receive one or more fingers therethrough, wherein one of said openings is adjacent said first receptacle member. Furthermore, such device further comprising a second receptacle member disposed the other of said ends, said second receptacle member being closed at said other of said ends of said body portion and open in the direction away from said other of said ends of said body portion, said second receptacle having a cavity sized and configured to receive and retain a fingertip; wherein said openings are configured as slits, slots or apertures; wherein said body portion is composed of a silicone material; wherein said body portion is approximately 60-80 cm in length and approximately 5-10 mm in width or diameter; wherein said first receptacle member is approximately 2-4 cm in length; and/or wherein said body portion is approximately 60-80 cm in length and approximately 5-10 mm in width or diameter, wherein said first receptacle member is approximately 2-4 cm in length, and wherein said openings are approximately 6-10 cm in length.

Alternatively, the invention is a method of treating should dystocia during childbirth comprising the steps of: providing a subaxillary traction device comprising a single, elongated body portion having two ends, said body portion composed of a flexible, pliable polymer material suitable for use in a medical or surgical procedure, wherein said body portion has a form chosen from the group of forms consisting of a strip, a strap, a cylindrical member and a tubular member; a first receptacle member disposed on one of said ends, said first receptacle member being closed at said one of said ends of said body portion and open in the direction away from said one of said ends of said body portion, said first receptacle having a cavity sized and configured to receive and retain a fingertip; said body portion having an opening in each of said ends, each of said openings extending through said body portion and sized to receive one or more fingers therethrough, wherein one of said openings is adjacent said first receptacle member; inserting a fingertip into said first receptacle member and introducing said one of said ends of said body portion into a vagina and around a posterior axilla of a fetus; grasping said one of said ends of said body portion, removing said fingertip from said first receptacle member and retrieving said one of said ends from said vagina such that said body portion remains positioned around the posterior axilla; inserting fingers through said openings and applying traction to said body portion, thereby flexing and shrugging the shoulder of the fetus to free the fetus; and pulling the posterior arm from the vagina whereby the fetus may be fully removed from the vagina.

BRIEF DESCRIPTION OF THE DRAWINGS

FIG. 1 is a view of a strap-like embodiment of the subaxillary traction device, the handle openings shown as slits.

FIG. 2 is a view of the device of FIG. 1 showing the handle openings in an expanded position.

DETAILED DESCRIPTION OF THE INVENTION

Figure 3:
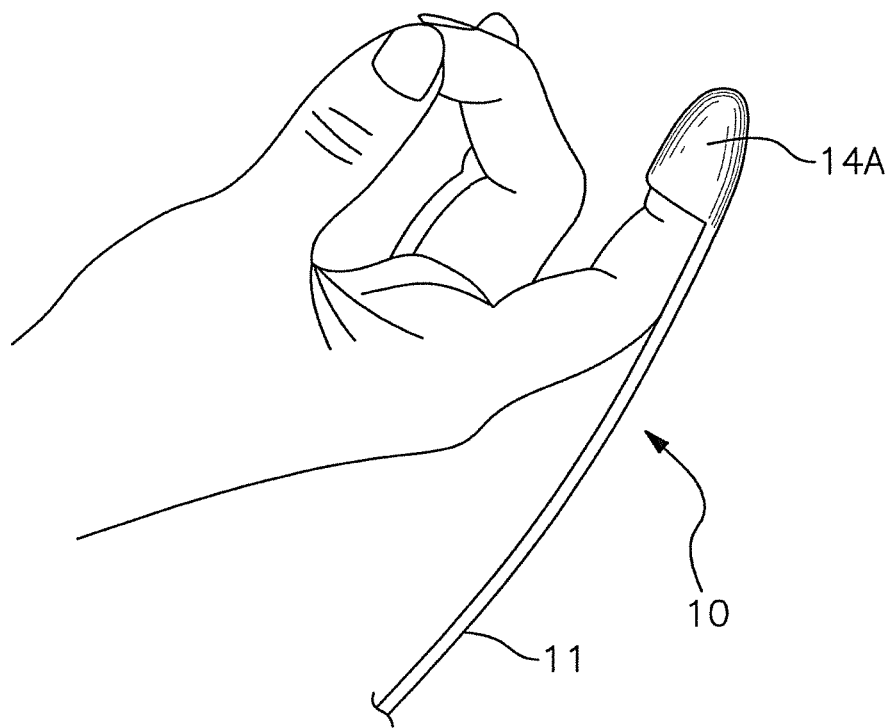
FIG. 3 is a partial view of a cylindrical embodiment of the device mounted to the index finger of the obstetrician in position for trans-vaginal insertion.
Figure 4:
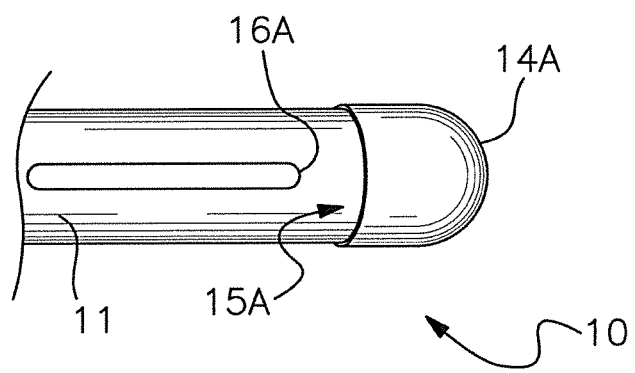
FIG. 4 is a partial view of an embodiment of the device showing the handle opening as a slot.

With reference to the drawings, the subaxillary traction device will now be described in detail with regard to multiple embodiments. The various embodiments as illustrated and described herein are not meant to be limiting, such that it is the intent that the scope of the invention be defined by the language of the claims.

As shown in the figures, the subaxillary traction device 10 comprises in general an elongated body portion 11 having a first end 12, a second end 13, at least one receptacle member 14 disposed on the first end 12, a handle opening 16 disposed adjacent or near the first end 12 and a handle opening 16 disposed adjacent or near the second end 13. Preferably a second receptacle member 14 is disposed on the second end 13. Although the traction device 10 may be composed of distinct materials bonded or otherwise connected, it is most preferable that the traction device 10 be composed of a single material that is flexible, pliable, non-rigid and supple. Most preferably the single material is a polymer material suitable for use in a medical/surgical environment, such as for example a silicone polymer. It is most preferable that the material of composition have a low friction surface and/or be suitable to receive and retain a lubricating coating.

The elongated body portion 11 of the traction device 10 is presented in the form of a thin strip, a thin strap, a small diameter cylinder or a small diameter tubing, with the material of composition and the cross-sectional dimensions being such that the body portion 11 is easily bent, flexed, looped and/or turned back upon itself, such that a first end 12 of the body portion 11 is easily introduced trans-vaginally during the delivery process, passed beneath the posterior axilla of the fetus, and then pulled out trans-vaginally, the length of the body portion 11 being such that both the first end 12 and the second end 13 may be gripped by the obstetrician externally to the vagina. As a representative and non-limiting example, the elongated body portion 11 may be formed as a length of cylindrical or tubular polymer material approximately 60-80 cm in length and possessing a width or diameter of approximately 5-10 mm. The terminology "elongated body portion" as used herein shall be taken as excluding and extraneous structure or elements that would interfere with or make more difficult introduction and passage of the first end 12 of the elongated body portion 11 into a vagina, around a posterior axilla of a fetus, grasping the inserted first end 12 and removing the first end 12 from the vagina.

The first end 12 of the body portion 11, being designated as the end to be introduced trans-vaginally, is provided with a receptacle member 14 in the form of a hood, cap, cup, sheath of the like that is sized and structured so as to present a cavity 15 able to temporarily receive the tip or end of the obstetrician's finger, as shown in FIG. 3. The receptacle member 14 is closed at the first end 12 and open in the direction away from the first end 12 of the traction device 10 and toward the bulk of the body portion 11 or second end 13, and may for example be approximately 2-4 cm in length. The receptacle member 14 may be structured or composed so as to be somewhat elastic in order to more securely grip the fingertip, such as for example similar in functionality to a finger cot formed of an elastic polymer. With this design, the first end 12 is easily and securely guided into the vagina and beneath the posterior axilla of the fetus. A second receptacle member 14 may be provided on the second end 13 of the body portion 11, such that either first end 12 or second end 13 may be utilized to position the traction device 10. The second receptacle member 14 defines a cavity 15 closed at the second end 13 and open in the direction of the first end 12.

Most preferably, a pair of handle openings 16 are disposed on the body portion 11 of the traction device 10. The handle openings 16 are fenestrations in the form of slits, slots, apertures or other open shapes that are sized such that at least one and preferably two or more fingers may be inserted there through. As a representative and non-limiting example, the handle openings 16 may be approximately 6-10 cm in length. The distance between the handle openings 16 is sufficient such that both handle openings 16 will reside externally to the vagina when the body portion has been positioned beneath the posterior axilla of the fetus and traction is to be applied. Preferably, one handle opening 16 is disposed adjacent or near the first end 12 and the other handle opening 16 is disposed adjacent or near the second end 13. The configuration of the handle opening 16 is preferably such that the size of opening remains closed or relatively small when the body portion 11 is non-stressed or under stress, such that the handle openings 16 will not impede or interfere with insertion and retrieval of the first end 12 of the body portion 11 as it is positioned around the posterior axilla.

To retrieve the first end 12 of the body portion 11 after it has been positioned around the posterior axilla of the fetus, the obstetrician may grip the first end 12 with fingers or forceps, may insert a hooked finger into the now empty receptacle member 14 of the first end 12, or may insert one or more fingers into the handle opening 16 adjacent the first end 12. Once the first end 12 is fully retrieved, both handle openings 16 are now positioned externally to the vagina and are accessible to the obstetrician.

Thus, in the event that shoulder dystocia occurs during a birth, the obstetrician obtains a traction device 10 and preferably lubricates the traction device 10 if it is not pre-lubricated. The obstetrician inserts a fingertip, usually of the index finger, into the cavity 15 of the receptacle member 14 and directs the first end 12 into the vagina. The first end 12 is then curled around the posterior axilla of the fetus so as to extend in the direction of the vaginal opening. The first end 12 is then gripped by the other hand or forceps and pulled from the vagina. The handle openings 16 are then brought together and one or more fingers are inserted such that the obstetrician may exert traction on the traction device to flex or shrug the posterior shoulder allowing the posterior arm to be delivered, relieving the trapped posterior shoulder, and thus allowing delivery of the baby.

It is understood that equivalents or substitutions for elements set forth above may be obvious to those of skill in the art, and therefore the true scope and definition of the invention is to be as set forth in the following claims.

I claim:

1. A method of treating shoulder dystocia during childbirth comprising the steps of:
   providing a subaxillary traction device comprising a single, elongated body portion comprising a first end and a second end, wherein the first end and the second end define extremities of the body portion such that the entire length of the body portion extends between the first end and the second end, the body portion comprising a flexible, pliable polymer material suitable for use in a medical or surgical procedure; and a first receptacle member disposed on the extremity of the body portion defined by the first end, the first receptacle member being closed at the first end of the body portion and open in the direction away from the first end of the body portion, the first receptacle member comprising a cavity sized and configured to receive and retain a fingertip;
   inserting a fingertip into the first receptacle member and introducing the first end of the body portion into a vagina and around a posterior axilla of a fetus; and
   grasping the first end of the body portion, removing the fingertip from the first receptacle member and retrieving the first end from the vagina such that the body portion remains positioned around the posterior axilla.

2. The method of claim 1, wherein the body portion of the subaxillary traction device comprises at least one opening in at least one of: the first end and the second end, the at least one opening extending through the body portion and sized to receive one or more fingers therethrough.

3. The method of claim 2, wherein when the at least one opening is in the first end, the at least one opening is adjacent to the first receptacle member.

4. The method of claim 2, wherein when the at least one opening is in the second end, the at least one opening is adjacent to a second receptacle member disposed on the extremity of the body portion defined by the second end, the second receptacle member being closed at the second end of the body portion and open in the direction away from the second end of the body portion, the second receptacle member comprising a cavity sized and configured to receive and retain a fingertip.

5. The method of claim 2, wherein the at least one opening is configured as at least one of: a slit, a slot, and an aperture.

6. The method of claim 2, wherein the at least one opening is approximately 6-10 cm in length.

7. The method of claim 2, the method further comprising:
inserting fingers through the at least one opening and applying traction to the body portion, thereby flexing and shrugging the shoulder of the fetus to free the fetus; and pulling the posterior arm from the vagina whereby the fetus may be fully removed from the vagina.

8. The method of claim 1, wherein the body portion of the subaxillary traction device comprises at least one of: a strip, a strap, a cylindrical member, and a tubular member.

\* \* \* \* \*